US00PP35770P2

(12) United States Plant Patent
Bull

(10) Patent No.: US PP35,770 P2
(45) Date of Patent: Apr. 23, 2024

(54) ***ECHINACEA* PLANT NAMED 'BULLECHIPUR 115'**

(50) Latin Name: *Echinacea purpurea*
Varietal Denomination: BullEchipur 115

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 18/378,823

(22) Filed: Oct. 11, 2023

Related U.S. Application Data

(60) Provisional application No. 63/475,160, filed on Oct. 20, 2022.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell
(74) *Attorney, Agent, or Firm* — The Webb Law Firm

(57) ABSTRACT

A new and distinct variety of *Echinacea* plant having an upright, very compact growth habit and numerous, magenta colored blooms.

1 Drawing Sheet

Botanical classification: *Echinacea purpurea.*
Varietal denomination: 'BullEchipur 115'.

BACKGROUND OF THE INVENTION

The present invention comprises a new and distinct cultivar of *Echinacea* plant known by the varietal name 'BullEchipur 115'. The new variety was discovered in August of 2019 in Gönnebek, Germany as the result of a planned breeding program with the purposes of providing *Echinacea* plants with magenta-pink colored inflorescences, a more compact growth habit, more uniformity, good branching, early flowering, good propagation, and increased suitability for small pot sizes when compared to prior *Echinacea* plants. The new variety is the result of a cross between an unpatented *Echinacea purpurea* variety having an internal breeder's reference of "BUL 2017-22" (female parent) and an unpatented *Echinacea purpurea* variety having an internal breeder's reference of "BUL 2017-19" (male parent) from the breeder's own collection. The new variety was first asexually reproduced via in-vitro tissue culture cuttings in Gönnebek, Germany in September of 2019. The new variety is similar to its parental varieties in botanical classification, but exhibits a different inflorescence color, more compact growth habit, and smaller leaves than both of its parental varieties. 'BullEchipur 115' also has increased branching, a shorter height, and earlier flowering than its female parent. Further, the new variety produces more inflorescences than its male parent.

When 'BullEchipur 115' is compared to *Echinacea purpurea* variety named 'PAS702917' (unpatented, marketed as "PowWow® Wild Berry"), 'BullEchipur 115' is similar to 'PAS702917' in botanical classification, but 'BullEchipur 115' exhibits more compact, shorter growth with increased branching, more inflorescences per plant that are also of a uniform color, and more healthy, smaller leaves that distinguish it from 'PAS702917'. Further, the following characteristics distinguish 'BullEchipur 115' when generally compared to other *Echinacea* varieties known to the breeder:

An upright, very compact growth habit that is suitable for small pots;

Magenta ray floret color;
High inflorescence number per plant;
High branching;
A uniform growth habit;
Small leaves; and
A fast crop time.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWING

The accompanying photographic drawing illustrates the new variety at 21 weeks of age, with the color being as nearly true as is possible with color illustrations of this type.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 15 cm (1.5 liter) pots under normal field production conditions, and the color readings and measurements were observed outdoors under natural light on 21 week old plants in Gönnebek, Germany. Color references are primarily to the 2015 R.H.S. Colour Chart of The Royal Horticultural Society of London, Sixth Edition, except where terms of ordinary significance are used.

PLANT

Time to initiate roots: About 7 days at approximately 19-20° C.

Time to develop roots: About 40-50 days at approximately 18° C.

Time to produce a finished flowering plant from a rooted cutting: About 11-12 weeks in a 15 cm container.
Rooting habit: Exhibits numerous roots that are freely branching and healthy in appearance.
Plant height: 30.0-40.0 cm.
Plant width: 30.0-35.0 cm.
Habit: Upright, very compact growth with numerous branches.
Disease/pest resistance: Nothing unusual noted to date.
Temperature tolerance: Nothing unusual noted to date.
Drought tolerance: Average.
Branches (flowering stems):
*Number per plant.*—20-30.
*Length.*—15.0-25.0 cm.
*Diameter.*—3.0-7.0 mm.
*Internode length.*—1.0-3.0 cm.
*Angle.*—Upright and outward.
*Strength.*—Strong.
*Texture.*—Pubescence present.
*Color.*—Close to Greyed-Purple Group RHS 183B.
Foliage:
*Arrangement.*—Single.
*Leaf.*—Length: 4.0-15.0 cm. Width: 1.0-4.0 cm. Shape: Lanceolate. Apex: Acuminate. Base: Attenuate to acute. Margin: Entire. Aspect: Straight to curved. Texture: Upper surface: Rough. Lower surface: Rough. Color: Young leaves: Upper surface: Close to Green Group RHS 137A. Lower surface: Close to Green Group RHS 137C. Mature leaves: Upper surface: Close to Green Group RHS 137A. Lower surface: Close to Green Group RHS 137C. Petiole: None present. Veins: Venation type: Cross-venulate to longitudinal. Color: Upper surface: Close to Yellow-Green Group RHS 145A. Lower surface: Close to Yellow-Green Group RHS 145B.

INFLORESCENCE

Bud:
*Diameter.*—1.0-3.0 cm.
*Length.*—1.5-2.0 cm.
*Color.*—Close to Greyed-Purple Group RHS N187A.
Appearance: Elliptic-shaped ray florets and tubular-shaped disc florets.
Natural flowering season: Flowering occurs from July-September in Gönnebek, Germany, beginning approximately 11-12 weeks after planting.
Average number of inflorescences per plant: 20-30.
Average number of inflorescences per branch: 1-2.
Disc and ray floret arrangement: Disc florets are arranged in the middle of the receptacle of the composite, single, freely flowering plant, with ray florets extending outwardly therefrom.
Fragrance: None.
Inflorescence:
Disc type: Daisy.
*Diameter.*—4.0-8.0 cm.
*Height (depth).*—2.0-4.0 cm.
*Diameter of disc.*—1.5-3.5 cm.
*Receptacle height.*—1.0 cm.
*Receptacle diameter.*—1.5-2.5 cm.
Ray florets:
*Number per inflorescence.*—13-25.
*Arrangement.*—In two or three whorls.
*Length.*—1.6-3.5 cm.
*Width.*—0.8-1.5 cm.
*Shape.*—Elliptical.
*Apex.*—Obtuse.
*Base.*—Acute.
*Margin.*—Entire.
*Texture.*—Upper surface: Smooth and glabrous. Lower surface: Rough.
*Color.*—When opening: Upper surface: Close to Red-Purple Group RHS 60B. Lower surface: Close to Red-Purple Group RHS 60C. At maturity: Upper surface: Close to Red-Purple Group RHS 61A. Lower surface: Close to Red-Purple Group RHS 60B. Ground color description: Close to Red-Purple Group RHS 61A.
*Venation.*—Appearance: Parallel. Color: Upper surface: Same color as the florets. Lower surface: Same color as the florets.
Disc florets:
*Number per inflorescence.*—Numerous; too many to quantify.
*Arrangement.*—In the center of receptacle.
*Length.*—8.0-12.0 mm.
*Width.*—1.0-2.0 mm.
*Shape.*—Tubular.
*Apex.*—Pointed.
*Color.*—Immature: Close to Greyed-Purple Group RHS 187B. At maturity: Close to Red-Purple Group RHS 59B.
Phyllaries:
*Number per inflorescence.*—40-55.
*Arrangement.*—In 3-4 whorls.
*Length.*—Approximately 0.5-1.0 cm.
*Width.*—2.0-4.0 mm.
*Shape.*—Lanceolate.
*Apex.*—Elongated oval.
*Base.*—Fused.
*Margin.*—Entire.
*Texture.*—Upper surface: Rough. Lower surface: Rough.
*Color.*—Immature: Upper surface: Close to Green Group RHS NN137C. Lower surface: Close to Green Group RHS NN137C. At maturity: Upper surface: Close to Green Group RHS NN137C. Lower surface: Close to Green Group RHS NN137C.
Reproductive organs:
Androecium:
*Presence.*—On disc florets.
*Number (per floret).*—One.
*Filament length.*—1.0-2.0 mm.
*Filament color.*—Close to Greyed-Purple Group RHS 183B.
*Anther.*—Shape: Oval. Length: 1.0 mm. Color: Close to Greyed-Purple Group RHS 183B.
*Pollen.*—Color: Close to Yellow-Orange Group RHS 15B. Amount: Little, but difficult to quantify.
Gynoecium:
*Presence.*—In disc and ray florets.
*Pistil length.*—1.0-2.0 mm.
*Stigma.*—Shape: Two-parted. Color: Close to Red-Purple Group RHS 60C.
*Style.*—Length: 1.0-2.0 mm. Color: Close to Red-Purple Group RHS 60C. Seeds:
*Overall size.*—1.0 mm in width and 2.0 mm in length.

I claim:

1. A new and distinct variety of *Echinacea* plant named 'BullEchipur 115', as is herein illustrated and described.

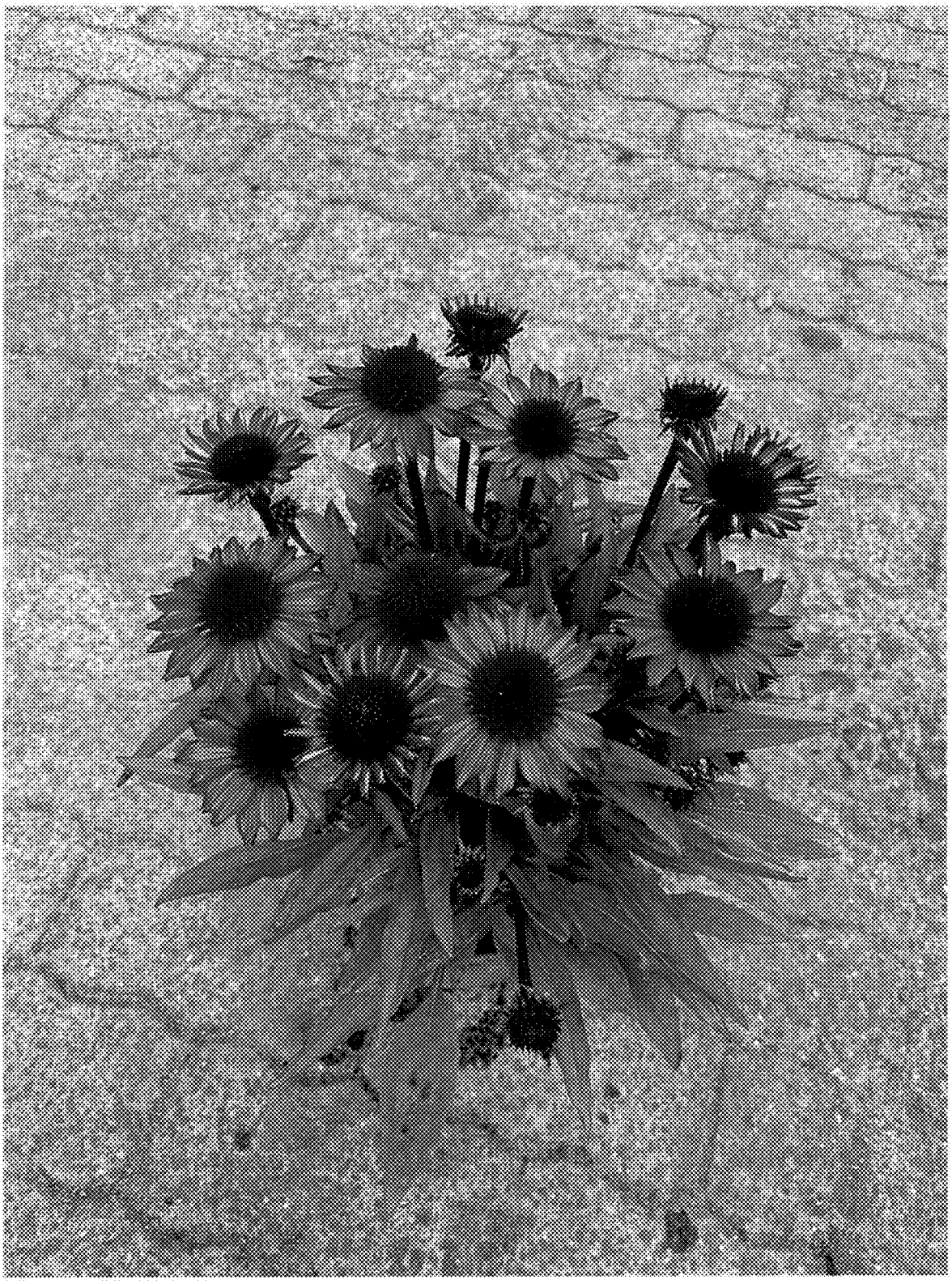

* * * * *